(12) United States Patent
Leussler (10) Patent No.: US 10,448,996 B2
(45) Date of Patent: Oct. 22, 2019

(54) ELECTROSURGICAL ABLATION APPARATUS

(71) Applicant: KONINKLIJKE PHILIPS N.V., Eindhoven (NL)

(72) Inventor: Christoph Leussler, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1513 days.

(21) Appl. No.: 14/368,891

(22) PCT Filed: Dec. 22, 2012

(86) PCT No.: PCT/IB2012/057660
§ 371 (c)(1),
(2) Date: Jun. 26, 2014

(87) PCT Pub. No.: WO2013/098757
PCT Pub. Date: Jul. 4, 2013

(65) Prior Publication Data
US 2014/0378958 A1    Dec. 25, 2014

Related U.S. Application Data

(60) Provisional application No. 61/581,119, filed on Dec. 29, 2011.

(30) Foreign Application Priority Data

Dec. 29, 2011    (EP) .................................... 11196043

(51) Int. Cl.
*A61B 18/18* (2006.01)
*A61B 18/00* (2006.01)

(52) U.S. Cl.
CPC .......... *A61B 18/18* (2013.01); *A61B 18/1815* (2013.01); *A61B 2018/00005* (2013.01);
(Continued)

(58) Field of Classification Search
CPC ................ A61B 18/18; A61B 18/1815; A61B 2018/00005; A61B 2018/00577; A61B 2018/1846
See application file for complete search history.

(56) References Cited

U.S. PATENT DOCUMENTS

| 5,246,438 A | 9/1993 | Langberg |
| 8,968,288 B2 | 3/2015 | Brannan |

(Continued)

FOREIGN PATENT DOCUMENTS

| CN | 2789949 Y | 5/2009 |
| CN | 101431186 A | 5/2009 |

(Continued)

*Primary Examiner* — Joseph M Dietrich (57) ABSTRACT

An electrosurgical ablation apparatus for generating and emitting electromagnetic radiation energy for ablating biological tissue is disclosed. The apparatus comprises an operating unit (1), a handheld applicator unit (3) with an applicator antenna (4) and a cable connection (2) between both. The applicator antenna (4) is a dual or multi-resonant ablation antenna (41a, ... 41d) for transmitting microwave ablation energy at at least two different frequencies which are selected especially according to the electrical properties and dimensions of the tissue to be ablated.

8 Claims, 7 Drawing Sheets

(52) U.S. Cl.
CPC ............... *A61B 2018/00577* (2013.01); *A61B 2018/1846* (2013.01); *A61B 2018/1869* (2013.01); *A61B 2018/1876* (2013.01)

(56) References Cited

U.S. PATENT DOCUMENTS

| | | |
|---|---|---|
| 2003/0065317 A1 | 4/2003 | Rudie et al. |
| 2010/0004650 A1* | 1/2010 | Ormsby ............. A61B 18/1492 606/41 |
| 2010/0125269 A1 | 5/2010 | Emmons et al. |
| 2010/0145328 A1 | 6/2010 | Hancock et al. |
| 2010/0286681 A1 | 11/2010 | Podhajsky |
| 2010/0286682 A1 | 11/2010 | Podhajsky |
| 2011/0208177 A1* | 8/2011 | Brannan ............ A61B 18/1815 606/33 |
| 2014/0378958 A1 | 12/2014 | Leussler |

FOREIGN PATENT DOCUMENTS

| | | |
|---|---|---|
| EP | 2324788 A1 | 5/2011 |
| EP | 2361582 A1 | 8/2011 |
| WO | 2011010089 A1 | 1/2011 |

\* cited by examiner

ELECTROSURGICAL ABLATION APPARATUS

This application is a national stage application under 35 U.S.C. § 371 of International Application No. PCT/IB2012/057660 filed on Dec. 22, 2012 and published in the English language on Jul 4, 2013 as International Publication No. WO/2013/098757, which claims priority to U.S. Application No. 61/581,119 filed on Dec. 29, 2011, and EP Application No. 11196043.1 filed on Dec. 29, 2011, the entire disclosures of which are incorporated herein by reference.

FIELD OF THE INVENTION

The invention relates to an electrosurgical ablation apparatus for generating and emitting electromagnetic radiation energy for ablating biological tissue. Further, the invention relates to a method for electrosurgical ablation under MR imaging control.

BACKGROUND OF THE INVENTION

Electromagnetic radiation, especially in the frequency range of microwaves, is frequently used for electrosurgical or hyperthermia therapy in order to ablate or coagulate distinct targeted areas or volumes (especially lesions) of a biological tissue in order to treat various diseases.

In this respect, electromagnetic radiation can effectively heat a tissue especially in at least one of two ways, namely by inducing an electric current in the tissue (if it is electrically conductive), or by inducing a rotation of the dipoles present in water molecules in the tissue (dielectric heating), wherein the rotation of the dipoles changes with changes in the electromagnetic radiation so that due to internal friction in the tissue cells, each dipole becomes a heating source.

US 2010/0145328 discloses an electrosurgical ablation apparatus and a method of ablating biological tissue. The apparatus comprises a handheld microwave subassembly which generates and amplifies a microwave signal for treatment, and includes a treatment antenna for delivering the microwave signal in the form of microwave radiation into the targeted tissue. Further, the subassembly comprises diode detectors for detecting forward and reflected power levels to enable determination of net delivered power. A dynamic impedance matching system may be provided to match energy developed by the amplifiers in the subassembly to the biological tissue load.

SUMMARY OF THE INVENTION

It has been revealed that the controlling of an ablation process with respect to a desired uniform heating of a desired targeted volume of a tissue to be ablated is sometimes more or less ineffective especially if for example along one side of the volume more blood vessels run (or run closer along this side) than along the other sides, so that the related one side of the targeted volume is cooled by the passing blood to a greater extent than the other sides of the targeted volume. By this, the efficiency of the ablation process is decreased because the complete ablation of a certain volume of a tissue requires a certain increased and uniform temperature which, however, should not be exceeded considerably in order not to affect other parts of surrounding or adjacent tissue which are not to be ablated or treated.

Further, even in case of a substantially uniform dissipation of heat in or from the surroundings of a desired targeted volume, a uniform heating of a targeted volume can be impaired or restricted and the efficiency of the ablation process is accordingly decreased when this volume is not at least substantially spherical, but has for example non symmetrical or arbitrary or irregular extensions.

An object underlying the invention is to provide an electrosurgical ablation apparatus, by means of which the efficiency of the ablation process can be improved especially in case of a non-uniform heat dissipation in or from the surroundings of the targeted tissue (which is usually a lesion), and/or if the targeted volume has a non-spherical or irregular extension.

This object is solved by an electrosurgical ablation apparatus according to claim 1.

Generally, the invention is based on the recognition that the efficiency of heating of a tissue and by this the efficiency of the ablation process depends not only on the power but especially on the frequency of the microwave radiation delivered into the tissue and that the efficiency of a certain frequency is dependent on certain physical properties of the tissue to be ablated. By using electromagnetic radiation having two or more different frequencies (especially in the microwave frequency range) at the same time and/or one after the other, additional degrees of freedom to control the ablation process are provided.

An advantage of an electrosurgical ablation apparatus according to the invention is, that either a plurality of tissue volumes having different sizes and/or different electrical properties can be ablated in parallel, or one volume of a tissue can be heated in different areas to different degrees in order to compensate e.g. different amounts of heat dissipation from the volume as explained above, in both cases by means of different and individually optimized frequencies of the electromagnetic radiation.

The dependent claims disclose advantageous embodiments of such an electrosurgical ablation apparatus.

It will be appreciated that features of the invention are susceptible to being combined in any combination without departing from the scope of the invention as defined by the accompanying claims.

Further details, features and advantages of the invention will become apparent from the following description of preferred and exemplary embodiments of the invention which are given with reference to the drawings.

DETAILED DESCRIPTION OF EMBODIMENTS

Figure 1:
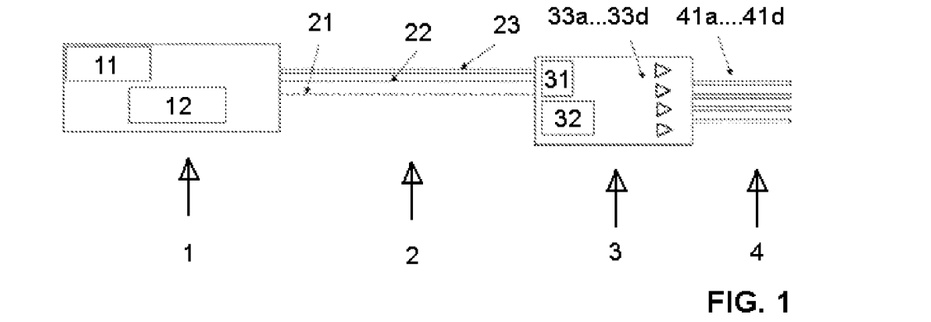
FIG. 1 schematically shows a first basic set-up of a multi-frequency electro surgical ablation apparatus.

FIG. 1 schematically shows a first basic set-up of an electrosurgical ablation apparatus for generating and emitting electromagnetic radiation energy, preferably in the microwave frequency range, in the form of RF ablation signals having two or more different RF frequencies into a targeted tissue or lesion to be ablated. Preferably, such frequencies are in the ranges of about 900 MHz, 2,4 GHz and up to about 9 to 12 GHz, usually according to the permitted ISM frequency ranges.

The apparatus substantially comprises an operating unit 1 (which is usually stationary unit), a handheld applicator unit 3 with an applicator antenna 4 (also called ablation antenna) and a cable connection 2 by means of which the handheld applicator unit 3 is connected with the operating unit 1.

The operating unit 1 comprises for example a control system 11 for controlling the applicator unit 3, especially for activating the generation of the RF ablation signals to be transmitted by the applicator antenna 4, and for selecting its power and frequency, and preferably a cooling system 12 for cooling the cable connection 2 and/or the applicator unit 3. Further systems like a power supply can be included into the operating unit 1.

The handheld applicator unit 3 preferably comprises at least one microwave generator and RF power amplifier 33$a$, . . . 33$d$ which is controlled by the control system 11 for generating and amplifying, respectively, RF ablation signals with a desired RF power and frequency to be transmitted by means of the applicator antenna 4 for the ablation of tissue.

Integrating the at least one microwave generator and RF power amplifier 33$a$, . . . 33$d$ into the handheld applicator unit 3 has the advantage that in comparison to integrating these components into the operating unit 1, no microwave (power) cable connection is necessary for connecting the operating unit 1 with the handheld applicator unit 3. By this, the cable connection 2 can be made longer, higher microwave frequencies can be used and no RF power losses occur as with conventional microwave cable connections, so that the RF power requirements are reduced and the freedom for the design of stand alone microwave ablation systems and combined therapy ablation e.g. inside a magnetic resonance imaging system is increased. Further components can be included into the applicator unit 3 like e.g. a display unit, a switch unit for manually switching on and off the RF power amplifiers 33$a$, . . . 33$d$, for selecting the RF power and/or frequency of the RF ablation signals to be transmitted, and other.

Further, the applicator unit 3 is provided with an applicator antenna 4. Generally, the applicator antenna 4 is provided for emitting electromagnetic radiation energy (i.e. the RF ablation signals) at at least two different frequencies, either in an alternating manner (i.e. sequentially) or at the same time (i.e. simultaneously), into a targeted volume of a tissue ("lesion"). In order to realize this, various solutions are proposed in the following, which can also be used in any combination with each other.

According to FIG. 1, the applicator antenna 4 exemplarily comprises a plurality of antenna needles 41$a$, . . . 41$d$. For the sake of clarity only, it is assumed in the following, that this antenna 4 comprises four antenna needles 41$a$, . . . 41$d$, however, these explanations accordingly apply for any other number of antenna needles.

The four antenna needles 41$a$, . . . 41$d$ are preferably mono-resonant, i.e. they are dimensioned to be resonant (preferably $\lambda/4$ resonant) at each one of four different frequencies. Therefore, microwave ablation can be conducted at a selected one or at up to four different frequencies at the same time by selecting and activating the related antenna needles. In the following, it is assumed that these frequencies are in the range of microwave frequencies as mentioned above.

Accordingly, the applicator unit 3 according to FIG. 1 comprises four microwave generators with RF power amplifiers 33$a$, . . . 33$d$ for the parallel feeding of the four antenna needles 41$a$, . . . 41$d$, respectively, with each one RF ablation signal having one of four different frequencies, for radiating RF ablation energy into the targeted tissue.

The applicator unit 3 and especially the microwave generators and RF power amplifiers 33$a$, . . . 33$d$, respectively, are preferably controlled for activation and selection of frequency and/or RF power level to be delivered to the antenna needles 41$a$, . . . .41$d$ by means of digital control signals (preferably in an optical format) which are generated by means of the control system 11 included in the operating unit 1. Accordingly, the cable connection 2 preferably comprises an optical fiber 22 for transmitting the related (optical) control signals.

For receiving and processing such digital control signals, the applicator unit 3 comprises a related interface 31 and preferably a programmable DDS 32 which distributes such digital control signals to the microwave generators and RF power amplifiers 33$a$, . . . 33$d$.

For supplying the applicator unit 3 with electrical power, the cable connection 2 comprises a DC power supply cable 21. Finally, the cable connection 2 preferably comprises a cooling line 23 for supplying a cooling medium, especially a liquid, from the cooling system 12 included in the operating unit 1 to the applicator unit 3 and back again in a known manner. Preferably, a temperature sensor is provided at the applicator unit 3 for sensing its temperature, wherein the sensor signal can be fed back via the optical fiber 22 to the control system 11 of the operating unit 1 in order to switch off the microwave generators and RF power amplifiers 33$a$, . . . 33$d$ when the temperature exceeds a certain maximum allowable threshold value.

Figure 2:
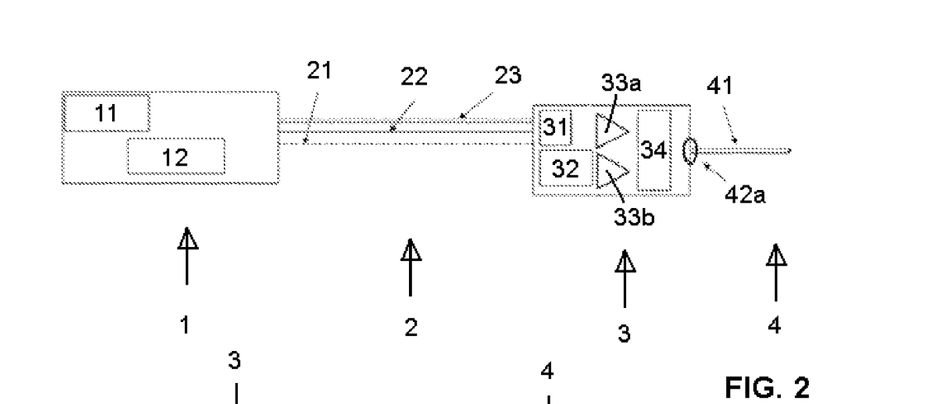
FIG. 2 schematically shows a second basic set-up of a multi-frequency electro surgical ablation apparatus.

FIG. 2 schematically shows a second basic set-up of an electro surgical ablation apparatus.

The same or corresponding units and components as in FIG. 1 are denoted in FIG. 2 with the same or corresponding reference signs. Accordingly, only the differences to the first embodiment shall be explained in the following.

In contrast to the first set-up, the applicator antenna 4 comprises only one antenna needle 41, which, however, is dimensioned to be dual- or multi-resonant, i.e. it can be excited to resonate (preferably at $\lambda/4$ wavelength) at two (or more) different microwave frequencies as explained below.

Accordingly, two (or more) microwave generators and RF power amplifiers 33a, 33b are provided for feeding the antenna needle 41 with RF ablation signals having two (or more) different microwave frequencies (and possible different RF power levels), which can be selected by a user and can be transmitted simultaneously or sequentially. Alternatively, one microwave generator or RF power amplifier can be provided which can be switched between the related two (or more) different microwave frequencies (and preferably RF power levels).

Alternatively, also two antenna needles could be provided, which are each dimensioned to be resonant at each for example two different resonant frequencies, so that in total four different resonant frequencies are available for ablation. Again, the microwave generators and RF power amplifiers 33a, . . . 33d, respectively, are preferably controlled for activation and selection of frequency and/or RF power to be delivered to the applicator antenna 4 by means of digital control signals which are submitted by the control system 11 as explained above.

Due to the different loading of the applicator antenna 4 especially when the antenna needles are partly or totally introduced into a tissue, preferably a tuning and matching device 34 is provided as generally known, with which the input impedance of the applicator antenna 4 is matched to the output impedance of the RF amplifiers 33a, 33b and accordingly tuned, so that no or only a minimum of the generated RF power is reflected at the ablation antenna 4. By this, the RF power is optimally transformed to thermal energy within the tissue. This of course applies for all disclosed and other embodiments of the applicator antenna 4 and the applicator unit 3, respectively.

Finally, FIG. 2 exemplarily shows an optional connector 42a for connecting the antenna needle 41 with a housing of the applicator unit 3 in such a way, that the antenna needle 41 can be easily separated by a user from the housing for disposal and exchange after use.

Figure 3:
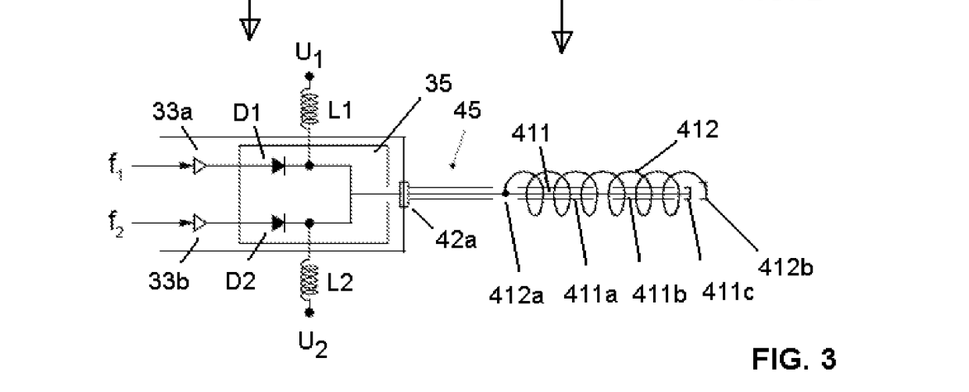
FIG. 3 schematically shows substantial components of an applicator unit and a dual resonant applicator antenna according to a first embodiment.

FIG. 3 schematically shows substantial components of an applicator unit 3 and a dual resonant applicator antenna 4 according to a first embodiment.

The applicator unit 3 exemplarily comprises a first RF power amplifier 33a, a second RF power amplifier 33b and a conventional PIN switch 35. The input of the first and the second amplifier 33a, 33b is each connected with a first and a second RF (microwave) signal generator (not indicated) for generating a first RF ablation signal having a first frequency $f_1$ and a second RF ablation signal having a second frequency $f_2$, respectively. These RF signals are amplified by the related first and second RF power amplifier 33a, 33b, respectively, as needed for the RF ablation of the related tissue. The output of the first and the second RF power amplifier 33a, 33b is connected with a first and a second PIN diode D1, D2, respectively, of the PIN switch 35. The first and the second PIN diode D1, D2 can be switched conductive or non-conductive by applying a related first and second bias voltage U1, U2, respectively, via a first and a second inductance L1, L2, respectively, in order to apply the amplified first or second RF ablation signal at the applicator antenna 4.

The applicator antenna 4 is a dual resonant antenna (again preferably at λ/4 wavelength), substantially in the form of a helix antenna, having a first resonator element 411 for transmitting the first RF ablation signal at the first frequency $f_1$ and a second resonator element 412 for transmitting the second RF ablation signal at the second frequency $f_2$.

The first resonator element 411 is a coaxial conductor structure comprising an inner conductor and an outer RF shield. The second resonator element 412 is provided by a (helical) coil which is wound around the first resonator element 411, wherein the proximal end 412a of the coil is connected with the inner conductor of the coaxial conductor structure. The distal end 412b of the coil and the distal end 411c of the coaxial conductor structure, namely of the inner conductor and of the RF shield, are electrically isolated from one another, preferably by fixing the same at a common carrier which is made from an electrically isolating material.

The RF shield of the coaxial conductor structure is realized in the form of two or more shielding stubs 411a, 411b which are electrically isolated form one another and which are dimensioned with respect to their axial length and diameter and distance from one other for tuning the desired first and second resonant frequency and/or for obtaining a more homogeneous current distribution along the resonator elements 411, 412 of the dual resonant applicator antenna 4. Preferably, the first resonator element 411 is tuned at a higher of the two microwave ablation frequencies in comparison to the second resonator element 412, which latter is especially realized as a quarter wave antenna.

For ease of introduction of the applicator antenna 4 into a tissue, the first and the second resonator elements 411, 412 are preferably surrounded by a common sleeve (not indicated) which is made from an electrically isolating material.

The dimensioning of the first and the second resonator element 411, 412, namely its axial lengths and diameters, the number of windings or inductance of the coil and the dimensioning of the shielding stubs, is calculated in dependence on the selected first and second microwave ablation frequency preferably by means of a known EM simulation program.

Finally, the applicator antenna 4 comprises a coaxial feeding section 45 by means of which the antenna is connected with the applicator unit 3. Preferably, the applicator antenna 4 is again fastened at a housing of the applicator unit 3 by means of a connector 42a as explained above with reference to FIG. 2 in order to easily remove and exchange the applicator antenna 4 after use.

Figure 4:
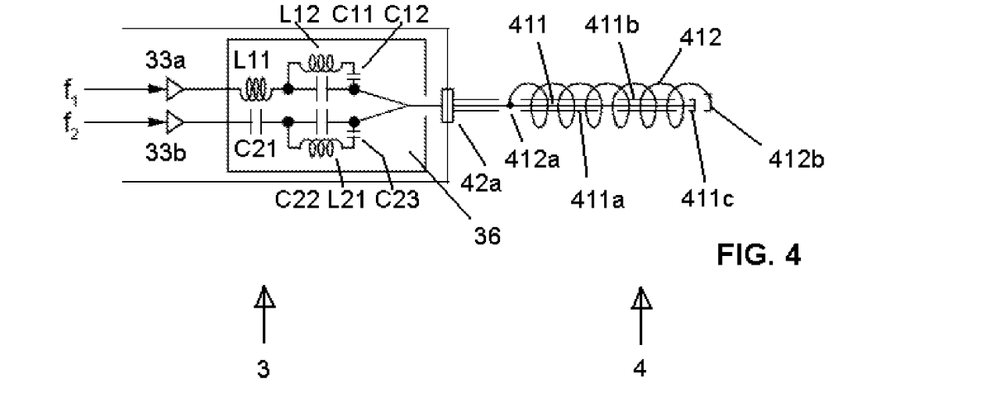
FIG. 4 schematically shows substantial components of an applicator unit and a dual resonant applicator antenna according to a second embodiment.

FIG. 4 schematically shows substantial components of an applicator unit 3 and a dual resonant applicator antenna 4 according to a second embodiment.

The same or corresponding parts and components as in the first embodiment according to FIG. 3 are denoted with the same or corresponding reference signs. In the following, substantially only the differences to the third embodiment shall be explained.

Instead of the PIN switch 35, the applicator unit 3 comprises a diplexer 36 in the form of a conventional diversity circuit. Such a circuit 36 has especially three functions, namely combining the first and the second RF ablation signal and decoupling the outputs of the first and the second amplifier 33a, 33b from one another, and matching the impedances at the outputs of the amplifiers to the impedance at the input of the RF ablation antenna. Consequently, this embodiment is especially suitable for simultaneously transmitting the first and the second RF ablation signal.

Again, the diplexer 36 comprises a first input which is connected with the output of the first amplifier 33a, and a second input which is connected with the output of the second amplifier 33b. Further, the diplexer 35 comprises one output which is connected with the applicator antenna 4. Between the first input and the output of the diplexer 35, a series connection of a first inductance L11 with a parallel connection of a first capacitor C11 with a second inductance L12 in series with a second capacitor C12 is connected.

Between the second input and the output of the diplexer 36, a series connection of a third capacitor C21 with a parallel connection of a fourth capacitor C22 with a third inductance L21 in series with a fifth capacitor C23 is connected. These capacitors and inductances are dimensioned in dependence on the first and the second frequency in a known manner such that the above three functions are fulfilled.

The ablation antenna 4 is preferably the same as the one as shown and explained with reference to the first embodiment according to FIG. 3.

Figure 5:
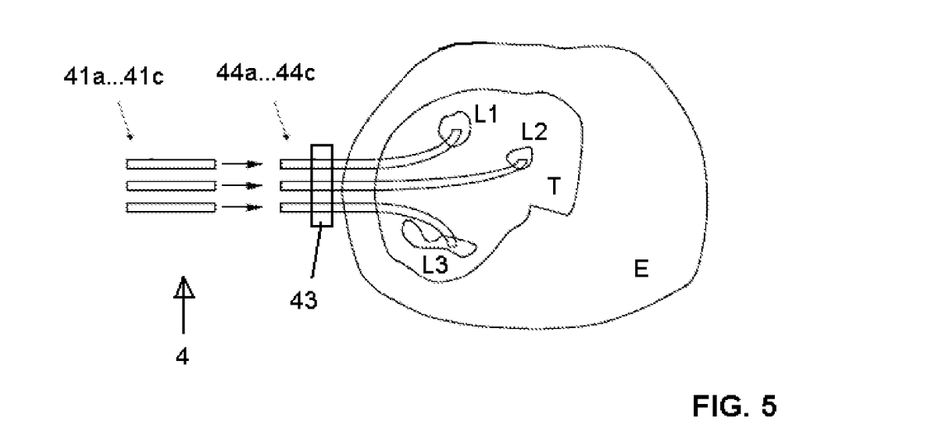
FIG. 5 schematically shows a distal end region of an ablation antenna and an organ.

FIG. 5 schematically shows an organism E which includes a certain organ T (e.g. a liver) having three lesions L1, L2, L3 (e.g. tumor tissues) with different sizes and different electrical properties which are to be ablated. For effectively ablating such different lesions, the frequency and/or the power of the RF ablation signal which is radiated into the related lesion should be selected appropriately especially in dependence on the size and the electrical properties and/or other parameters of the individual lesion.

For individually ablating each of the three (or a plurality of) lesions by means of each an individual RF ablation signal having an appropriately selected frequency and RF power level, the applicator antenna 4 comprises three (or a corresponding other number) of antenna needles 41a, . . . 41c (which each can be single- or multi-resonant) at which each the appropriate RF ablation signal for each one of the lesions is applied.

In order to make it easier to position the distal tips of the antenna needles 41a, . . . 41c at the corresponding lesion, at first each one flexible catheter 44a, . . . 44c is guided under MRI or ultrasound or x-ray control with its distal tip towards or into each one of the lesions L1, . . . L3. When the distal tips of the catheters have reached the related lesions (targeted tissue) to be ablated, the corresponding antenna needle 41a, . . . 41c is introduced into the lumen of each catheter 44a, . . . 44c until it reaches the distal tip of the catheter and by this the desired lesion. Preferably, the catheters 44a, . . . 44c are fixed to one another by means of a holder 43.

If the catheters 44a, . . . 44c are made from a flexible material, the distal end regions of the antenna needles 41a, . . . 41c to be introduced into the catheters are preferably also made from a flexible material.

Figure 6:
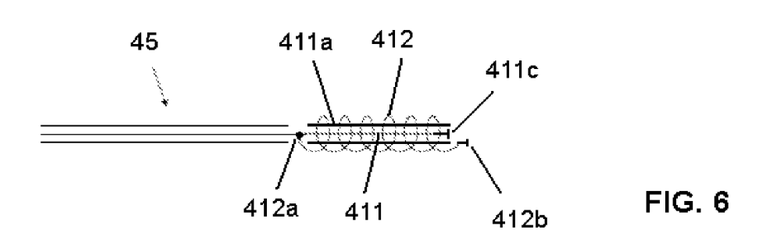
FIG. 6 schematically shows a third embodiment of an applicator antenna.

FIG. 6 schematically shows another embodiment of a dual resonant applicator antenna 4 which again comprises a coaxial feeding section 45 by means of which it is connected with an applicator unit 3.

The same or corresponding parts and components as in the embodiments according to FIGS. 3 and 4 are denoted with the same or corresponding reference signs. In the following, substantially only the differences to the these embodiments shall be explained.

The dual resonant antenna again comprises a first resonator element 411 for transmitting the first RF ablation signal at the first frequency $f_1$ and a second resonator element 412 for transmitting the second RF ablation signal at the second frequency $f_2$.

The first resonator element 411 is provided by a coaxial conductor structure comprising an inner conductor and an outer RF shield. The second resonator element 412 is provided by a (helical) coil which is wound around the first resonator element 411, wherein the proximal end 412a of the coil is connected with the inner conductor of the coaxial conductor structure.

Again, the distal end 412b of the coil and the distal end 411b of the coaxial conductor structure, namely of the inner conductor and of the RF shield, are electrically isolated from one another, preferably by fixing the same at a common carrier made from an electrically isolating material.

By providing the outer RF shield in the form of one shielding stub 411a, the antenna can be realized in the form of a tip resonator. Especially such an antenna can be realized in the form of a flexible antenna for use with catheters as shown in FIG. 5.

The dimensioning of the first and the second resonator element 411, 412, especially its axial lengths and diameters, the number of windings or inductance of the coil, is calculated in dependence on the selected first and second RF ablation frequency preferably by means of a known EM simulation program.

Figure 7:
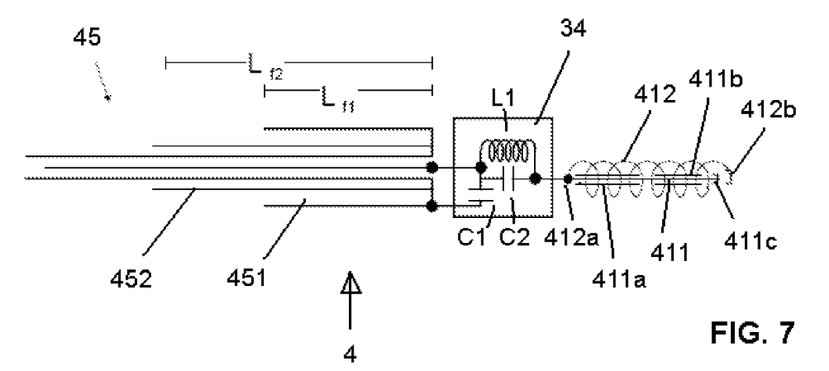
FIG. 7 schematically shows a fourth embodiment of an applicator antenna.

FIG. 7 schematically shows an embodiment of an applicator antenna 4 in which the coaxial feeding section 45 comprises a first and a second balun 451, 452 which coaxially surround the coaxial feeding section 45. The first balun 451 extends along a first (shorter) length Lf1 which is equal to about a quarter of the wavelength of the first (higher) frequency f and is tuned to be resonant at this first frequency f1. The second balun 452 extends along a second (longer) length Lf2 which is equal to about a quarter of the wavelength of the second (lower) frequency f2 and is tuned to be resonant at this second frequency f2. These baluns 451, 452 provide a high impedance to RF currents at the first and the second frequency f1, f2, respectively, of the distal dual resonant antenna 411, 412 and by this prevent a backward heating of the proximal feeding section 45 of the applicator antenna. Further, by limiting the RF currents on the feeding section 45, a more distinct radiation pattern for both frequencies f1, f2 can be provided.

The dual resonant antenna 411, 412 is preferably provided as shown in and explained above with respect to FIG. 3 or 6.

Between that coaxial feeding section 45 and the dual resonant antenna 411, 412, preferably a matching circuit 34 is connected (as explained above with reference to FIG. 2) which comprises a first capacitor C1 between the inner and the outer conductor of the coaxial feeding section 45. A parallel connection of a second capacitor C2 and a first inductance L1 is connected between the inner conductor of the coaxial feeding section 45 and the output of the matching circuit 34 which latter is connected with the applicator antenna 4. Alternatively, the matching circuit 34 can also be realized in a known manner by means of a strip line circuit instead of lumped elements.

By this matching circuit 34, the impedance at the output of the feeding section 45 is matched to the impedance at the input of the dual resonant antenna for the desired resonant frequencies. If necessary, such a matching circuit 34 can also be provided at any of the other embodiments in a known manner.

Figure 8:
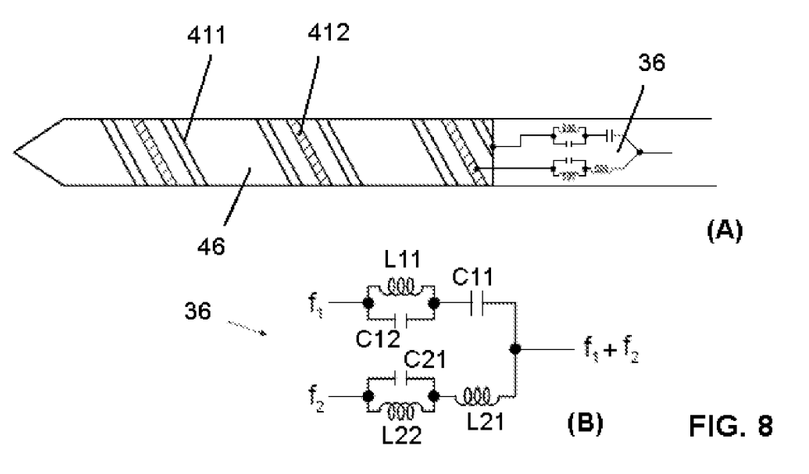
FIG. 8 schematically shows a fifth embodiment of an applicator antenna.

FIG. 8(A) schematically shows another embodiment of an applicator antenna 4 again in the form of a dual resonant antenna which comprises a first and a second resonator element in the form of a first conductor structure 411 which is resonant at a first microwave frequency and a second conductor structure 412 which is resonant at a second microwave frequency. The conductor structures are especially strip lines and are wound preferably parallel to each other around a cylindrical holder or carrier 46. Again, the dimensioning of the conductor structures 411, 412, especially their lengths and widths, the number of windings or inductances of the structures, is calculated in dependence on the selected first and second resonant frequency (again preferably at λ/4 wavelength) preferably by means of a known EM simulation program.

The carrier 46 is for example a rod having a circular or oval cross section and is made of a ceramic or a flexible material or another electrically isolating material. Such a carrier 46 can also be provided with inner channels through which a cooling medium like a liquid is fed for cooling the ablation antenna.

Further, FIG. 8(A) shows a diplexer 36, having an input which is connected with a feeding section at which both a first and a second RF ablation signal having a first and a second frequency f1, f2, respectively, is applied, wherein a first output of the diplexer 36 is connected with the first conductor structure 411 and a second output of the diplexer 36 is connected with the second conductor structure 412 of the applicator antenna 4.

The diplexer 36 is provided for decoupling and feeding the first and the second RF ablation signal to the first and the second conductor structure, respectively, and for matching the impedance of the feeding section to the impedance of the RF ablation antenna. The diplexer 36 is indicated in FIG. 8(B) in an enlarged scale. Between its input and the first output, the diplexer 36 comprises a series connection of a first capacitor C11 with a first inductance L11, to which latter a second capacitor C12 is connected in parallel. Between its input and the second output, the diplexer 36 comprises a series connection of a second inductance L21 and a third inductance L22, to which latter a third capacitor C21 is connected in parallel. These conductors and inductances are dimensioned in a known manner such that the first output is decoupled from the second output, and that at the first output only the first RF ablation signal and at the second output only the second RF ablation signal is applied in order to each excite the first and second resonances, respectively, on the first and the second conductor structure 411, 412, respectively. The diplexer 36 can be provided in a miniaturized form for example within the carrier 46.

Figure 9:
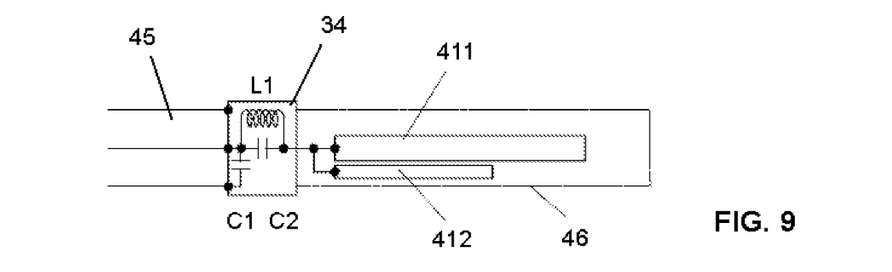
FIG. 9 schematically shows a sixth embodiment of an applicator antenna.

FIG. 9 schematically shows another embodiment of an applicator antenna 4, again in the form of a dual resonant antenna which comprises a first conductor structure 411 which is resonant (preferably λ/4 resonant) at a first microwave frequency and a second conductor structure 412 which is resonant (preferably λ/4 resonant) at a second microwave frequency. The conductor structures are applied onto a holder or carrier 46, preferably in parallel to each other, however, in contrast to the embodiment according to FIG. 8, extending in the longitudinal direction of the holder 46. The holder 46 can also be provided in the form of a flat holder like a printed circuit board. Again, the dimensioning of the conductor structures 411, 412, especially of their lengths and widths, is calculated in dependence on the selected first and second microwave ablation frequency and a desired decoupling from one another preferably by means of a known EM simulation program.

Further, FIG. 9 shows a matching circuit 34 which is preferably connected between a feeding section 45 and the proximal ends of the first and the second conductor structure 411, 412 of the RF ablation antenna as shown in FIG. 7. With respect to the function of this matching circuit 34 and its components, reference is made to the above explanations in connection with FIG. 7.

Figure 10:
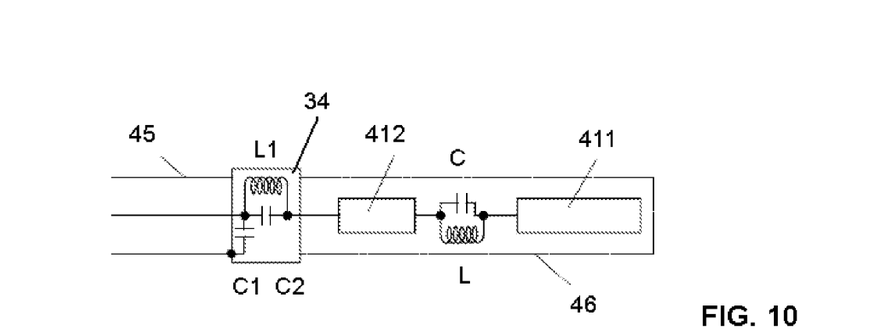
FIG. 10 schematically shows a seventh embodiment of an applicator antenna.

FIG. 10 schematically shows another embodiment of an applicator antenna 4 in which in contrast to the embodiment according to FIG. 9 the first and the second resonant conductor structures 411, 412 are connected in series, wherein a parallel resonant circuit in the exemplary form of a parallel connection of a capacitor C and an inductance L is connected between both conductor structures 411, 412. Further, FIG. 10 shows a matching circuit 34 as indicated in FIG. 9.

Figure 11:
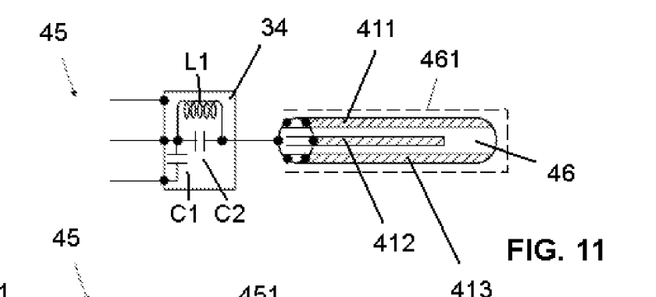
FIG. 11 schematically shows a eighth embodiment of an applicator antenna.

FIG. 11 shows another embodiment of an applicator antenna 4 in the form of a multi-resonant antenna which comprises at least a first, a second and a third conductor structure 411, 412, 413, which are each resonant (preferably λ/4 resonant) at a first, a second and a third microwave frequency, respectively. The conductor structures are applied onto a holder or a carrier 46 which in this example is realized in the form of a rod having a circular cross section. Also shown in this FIG. is an electrically isolating hosing 461 which preferably encloses the conductor structures as mentioned above. Further, FIG. 11 shows a matching circuit 34 as indicated in and explained with reference to FIG. 7.

Figure 12:
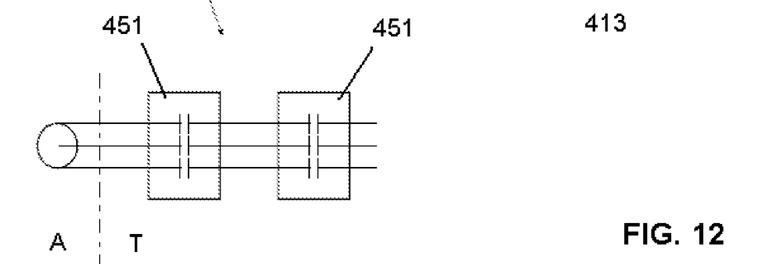
FIG. 12 schematically shows a ninth embodiment of an applicator antenna.

A preferred configuration of a feeding section 45 is shown in FIG. 12. This feeding section 45 (which can be used in connection with any other embodiment of the applicator antenna) is made to be substantially transparent in an MR image and by this is suitable for being introduced into a tissue T in which a lesson is to be ablated under MRI control.

The MR transparency is a obtained by connecting at least one capacitor 451 serially into each of the lines of the feeding section 45 (i.e. in case of a coaxial line into the RF shield and the inner conductor), wherein the capacitors are dimensioned such that the microwave ablation signals can pass the capacitors due to the low insertion loss at the microwave frequencies.

Figure 13:
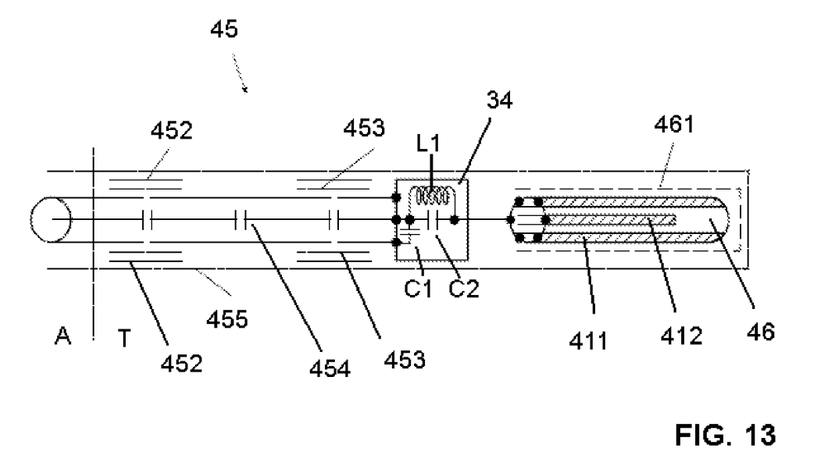
FIG. 13 schematically shows a tenth embodiment of an applicator antenna.

FIG. 13 shows a multi-resonant antenna and a matching circuit according to FIG. 11. Further, this FIG. shows a feeding section 45 in which MRI compatibility is obtained by providing a plurality of conductor sections which are connected by serial capacitors 454.

These capacitors 454 have an impedance which is low at the microwave ablation frequency and high at the much lower MRI frequency. The capacitors can be realized in the form of discrete capacitors 454 and/or by using foils and dielectric isolation material. Further, FIG. 13 shows an outer isolating cover 455 which surrounds the applicator antenna, wherein the feeding section 45 is coaxially surrounded by a dielectric material 453. This dielectric material 453 is coaxially surrounded by a metallic shield 452, on which the outer isolating cover 455 is applied.

Figure 14:
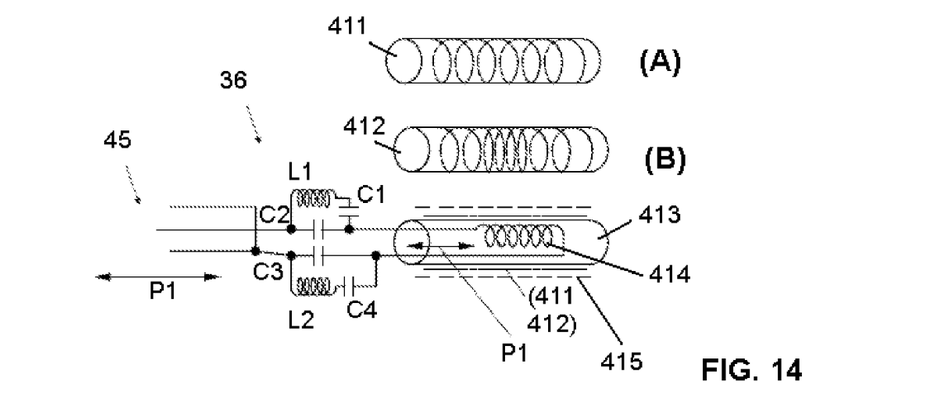
FIG. 14 schematically shows an eleventh embodiment of an applicator antenna.

FIG. 14 shows an embodiment of an applicator antenna in which the resonant conductor structures 411, 412 are inductively coupled to and by this galvanically decoupled from the feeding section 45.

The feeding section 45 comprises a coupling device in the form of an inductance 414 which is inserted into a tube element 413. On the outer surface of the tube element 413 the resonant conductor structures 411, 412 are applied which are exemplarily indicated in FIGS. 14(A) and 14(B) in the form of a first coil 411 having a first winding pattern and a second coil 412 having a second winding pattern, each for generating the first and the second ablation signal, respectively. The coils 411, 412 are preferably surrounded by a shield 415.

The first and the second ablation signal, which is supplied via the feeding section 45, is applied via a diversity switch 36 as explained in connection with FIG. 8 at the inductance 414 and inductively coupled into the resonant conductor structures 411, 412. For controlling the inductive coupling, it is preferred that the inductance 414 can be shifted within the tube element 413 in its axial direction as indicated by the arrow P1 in FIG. 14.

Figure 15:
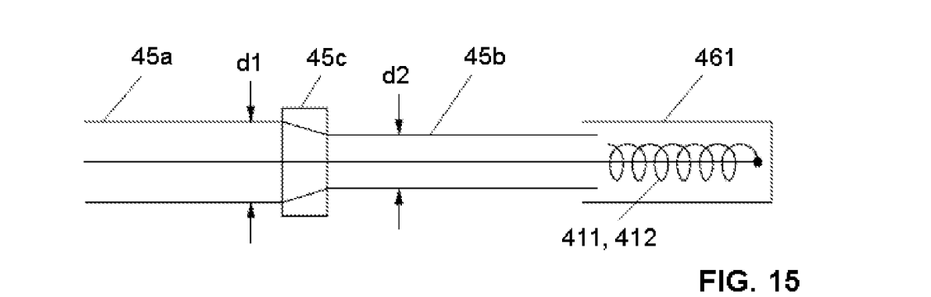
FIG. 15 schematically shows an exemplary embodiment of a feeding section.

FIG. 15 shows an embodiment of the feeding section 45. It comprises a first cable section 45a and a second cable section 45b which are connected with each other by means of a conventional connector 45c. The first cable section 45a is realized to have an especially low electric loss, wherein the second cable section 45b is realized to be especially flexible and preferably having an especially small diameter d2 (which is smaller than the diameter d1 of the low loss cable section 45a) in order to enable it to be introduced into a tissue. Finally, FIG. 15 schematically indicates an ablation antenna having a first and a second resonant conductor structure 411, 412 as explained above which is enclosed by an electrically isolating hosing 461 as explained above with reference to FIG. 11.

Figure 16:
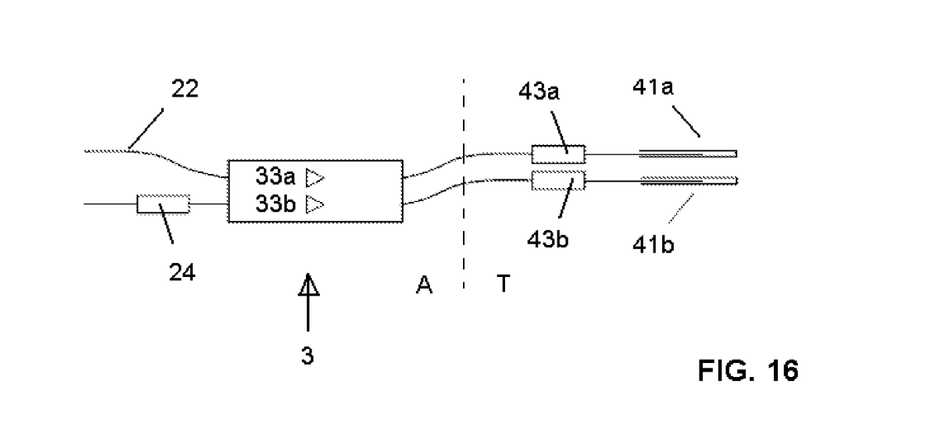
FIG. 16 schematically shows an arrangement of an applicator antenna adapted for use during MR imaging.

FIG. 16 generally shows an embodiment of a dual resonant applicator antenna which is especially provided for use during an MR examination in which the applicator antenna and the connected feeding lines are exposed to the RF/MR excitation field of the MR imaging apparatus. In order to prevent that common mode currents are induced on the antenna and propagate along the feeding lines, baluns 43a, 43b, 24 are provided for blocking such currents.

The embodiment shown in FIG. 16 comprises two single resonant applicator antennas or antenna needles 41a, 41b which are resonant at a first and a second microwave frequency, respectively. Accordingly, a first balun 43a is connected into a feeding line of the first antenna 41a, and a second balun 43b is connected into a feeding line of the second antenna 41b. The baluns 43a, 43b are suitable for being introduced in the related tissue.

Further, FIG. 14 shows a first and a second microwave generator and amplifier 33a, 33b for generating and amplifying a first and a second ablation signal, respectively, having the first and the second microwave frequency, respectively, which ablation signals are to be radiated by means of the first and the second antenna 41a, 41b, respectively. The microwave generators and amplifiers 33a, 33b are controlled preferably by means of an optical signal which is fed by means of an optical fiber 22, whereas a power supply is fed by means of a galvanic cable, into which a third balun 24 is connected.

Generally, the baluns 43a, 43b, 24 have a high impedance for the MR frequencies and a low insertion loss for the microwave ablation frequencies, and are a part of the related cable, such as a tri-axial coaxial cable as shown in FIG. 7, or the microwave cable is wound in the form of a solenoid and tuned using RF shield or capacitors according to the MR frequency.

Figure 17:
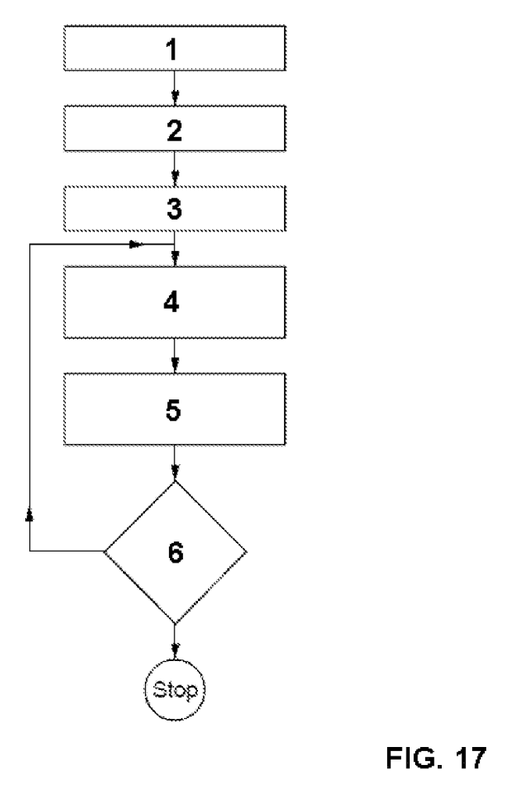
FIG. 17 a flowchart of an ablation procedure under MR imaging control.

FIG. 17 shows a flow chart of a microwave ablation procedure using a dual-resonant ablation antenna as disclosed above, wherein the procedure is preferably conducted under MRI control.

In a first step 1, an organ or tissue or a part of a body or volume which comprises the lesion to be ablated is imaged by means of an MR imaging procedure and segmented. In a second step 2, a model of the electromagnetic properties of the related volume is established. In a third step 3, a fast electromagnetic simulation of the ablation process is conducted on the basis of the electromagnetic model in order to evaluate appropriate values for frequencies, duty cycle and power for the microwave ablation process. These data are stored in a fourth step 4. Then, the actual microwave ablation process is started with a fifth step 5 using the data which have been stored in the fourth step 4. Preferably, the ablation process and the temperature development within the related tissue and other parameter are monitored in real time by MR imaging of the related tissue during a sixth step 6. If a predetermined threshold value of the temperature and/or of other parameters is exceeded, the related data which are stored and currently used for the ablation process are accordingly adapted. Finally, when the lesion is ablated, the ablation procedure is stopped.

While the invention has been illustrated and described in detail in the drawings and foregoing description, such illustration and description are to be considered illustrative or exemplary and not restrictive, and the invention is not limited to the disclosed embodiments. Variations to embodiments of the invention described in the foregoing are possible without departing from the scope of the invention as defined by the accompanying claims.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An electrosurgical ablation apparatus comprising an ablation antenna for emitting sequentially or simultaneously electromagnetic radiation energy having two or more different RF ablation frequencies for ablating biological tissue,
wherein the ablation antenna comprises at least one antenna needle which comprises a first and second resonator element which is resonant at a first and a second RF ablation frequency, respectively,
wherein the at least one antenna needle of the ablation antenna comprises a flexible antenna for use with catheters,
wherein the first resonator element is realized in the form of a coaxial conductor structure having an inner conductor and an outer RF shield, and the second resonator element is realized in the form of a helical coil which is wound around the coaxial conductor structure, and
wherein the proximal end of the helical coil of the second resonator element is connected with the inner conductor of the first resonator element and the distal end of the helical coil of the second resonator element is electrically isolated from the first resonator element.

2. The electrosurgical ablation apparatus according to claim 1, wherein the outer RF shield of the first resonator element is realized in the form of at least two shielding stubs which are electrically isolated from one another.

3. The electrosurgical ablation apparatus according to claim 1, wherein the at least one antenna needle is dimensioned to be resonant at a third and a fourth RF ablation frequency, first and second resonator element being realized in the form of each a helical coil which are applied onto an outer surface of a tube element.

4. The electrosurgical ablation apparatus according to claim 1, wherein the ablation antenna comprises the at least one antenna needle and a second antenna needle, wherein each of the at least one antenna needle and the second antenna needle is dimensioned to be resonant at two different resonant frequencies.

5. The electrosurgical ablation apparatus according to claim 1, wherein the first resonator element is tuned at a higher of the two or more different RF ablation frequencies in comparison to the second resonator element.

6. The electrosurgical ablation apparatus according to claim 1, further comprising:

an applicator unit coupled to the ablation antenna comprising at least one microwave generator and an RF power amplifier.

7. The electrosurgical ablation apparatus according to claim 6, further comprising:
   a control system controlling the applicator unit for generating and amplifying RF ablation signals to be transmitted by means of the ablation antenna.

8. The electrosurgical ablation apparatus according to claim 7, further comprising
a coaxial feeding section by means of which the ablation antenna is connected with the applicator unit.

* * * * *